US011802980B2

(12) United States Patent
Kato et al.

(10) Patent No.: US 11,802,980 B2
(45) Date of Patent: Oct. 31, 2023

(54) RADIATION DETECTOR, RADIOGRAPHIC IMAGING APPARATUS, AND MANUFACTURING METHOD

(71) Applicant: FUJIFILM Corporation, Tokyo (JP)

(72) Inventors: Munetaka Kato, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 356 days.

(21) Appl. No.: 17/214,003

(22) Filed: Mar. 26, 2021

(65) Prior Publication Data

US 2021/0215836 A1 Jul. 15, 2021

Related U.S. Application Data

(63) Continuation of application No. PCT/JP2019/037218, filed on Sep. 24, 2019.

(30) Foreign Application Priority Data

Sep. 27, 2018 (JP) .................................. 2018-182729

(51) Int. Cl.
*G01T 1/20* (2006.01)
*A61B 6/00* (2006.01)

(52) U.S. Cl.
CPC ........ *G01T 1/20181* (2020.05); *A61B 6/4283* (2013.01); *G01T 1/20189* (2020.05)

(58) Field of Classification Search
CPC .............. A61B 6/4283; G01T 1/20181; G01T 1/20189
See application file for complete search history.

(56) References Cited

U.S. PATENT DOCUMENTS

| | | |
|---|---|---|
| 2004/0104365 A1 | 6/2004 | Imai |
| 2007/0075247 A1 | 4/2007 | Mochizuki |
| 2012/0025084 A1 | 2/2012 | Virshup et al. |
| 2012/0219114 A1 | 8/2012 | Iwakiri et al. |
| 2013/0043400 A1 | 2/2013 | Nakatsugawa et al. |
| 2013/0154039 A1 | 6/2013 | Furui et al. |

(Continued)

FOREIGN PATENT DOCUMENTS

| | | |
|---|---|---|
| EP | 3 770 641 A1 | 1/2021 |
| JP | 2000-131444 A | 5/2000 |

(Continued)

OTHER PUBLICATIONS

An Office Action; "Notice of Reasons for Refusal", mailed by the Japanese Patent Office dated Apr. 26, 2022, which corresponds to Japanese Patent Application No. 2020-549201 and is related to U.S. Appl. No. 17/214,003; with English language translation.

(Continued)

*Primary Examiner* — Mark R Gaworecki
(74) *Attorney, Agent, or Firm* — Studebaker & Brackett PC

(57) ABSTRACT

Provided is a radiation detector including a substrate including a sensor unit layer having a plurality of pixels for accumulating electric charges generated depending on light converted from radiation in a pixel region of a flexible base material; a conversion layer that is provided on a surface side of the base material provided with the pixel region to convert the radiation into light; and a fixing member that is provided closer to the substrate side than the conversion layer to fix the sensor unit layer to the base material.

15 Claims, 10 Drawing Sheets

(56) References Cited

U.S. PATENT DOCUMENTS

| | | |
|---|---|---|
| 2015/0144889 A1 | 5/2015 | An et al. |
| 2015/0204987 A1 | 7/2015 | Okada et al. |
| 2016/0293285 A1 | 10/2016 | Fujiwara et al. |
| 2019/0298282 A1 | 10/2019 | Kato et al. |

FOREIGN PATENT DOCUMENTS

| | | |
|---|---|---|
| JP | 2003-017678 A | 1/2003 |
| JP | 2003-051586 A | 2/2003 |
| JP | 2004-172375 A | 6/2004 |
| JP | 2007-192807 A | 8/2007 |
| JP | 2010-076438 A | 4/2010 |
| JP | 2012-133315 A | 7/2012 |
| JP | 2014-218056 A | 11/2014 |
| JP | 2015-121425 A | 7/2015 |
| JP | 2016-136160 A | 7/2016 |
| TW | 201525515 A | 7/2015 |
| WO | 2011/148960 A1 | 12/2011 |
| WO | 2018/124134 A1 | 7/2018 |

OTHER PUBLICATIONS

International Search Report issued in PCT/JP2019/037218; dated Dec. 17, 2019.

International Preliminary Report on Patentability and Written Opinion issued in PCT/JP2019/037218; dated Mar. 23, 2021.

The extended European search report issued by the European Patent Office dated Oct. 21, 2021, which corresponds to European Patent Application No. 19867487.1-1001 and is related to U.S. Appl. No. 17/214,003.

An Office Action mailed by Taiwan Intellectual Property Office dated Jun. 5, 2023, which corresponds to Taiwanese Patent Application No. 108134759 and is related to U.S. Appl. No. 17/214,003; with partial English language translation.

RADIATION DETECTOR, RADIOGRAPHIC IMAGING APPARATUS, AND MANUFACTURING METHOD

CROSS-REFERENCE TO RELATED APPLICATION

This application is a continuation of International Application No. PCT/JP2019/037218, filed on Sep. 24, 2019, which claims priority to Japanese Patent Application No. 2018-182729, filed on Sep. 27, 2018. The entire disclosures of both of the above-referenced applications are hereby incorporated by reference into the present application.

BACKGROUND

Technical Field of the Invention

The present disclosure relates to a radiation detector, a radiographic imaging apparatus, and a manufacturing method.

Related Art

Radiographic imaging apparatuses that perform radiographic imaging for medical diagnosis are present. A radiation detector for detecting radiation transmitted through a subject and generating a radiographic image is used for such radiographic imaging apparatuses.

As this type of radiation detector, there is one comprising The substrate in which a conversion layer such as a scintillator that converts radiation into light and a sensor unit layer having a plurality of pixels that accumulate electric charges generated depending on the light converted by the conversion layer are provided in a pixel region of a base material (refer to, for example, JP2000-131444A, JP-2007-192807A, and JP2004-172375A).

As the base material of the substrate of such a radiation detector, one using a flexible base material is known. By using the flexible base material, for example, the weight of the radiographic imaging apparatuses (radiation detector) can be reduced, and a subject may be easily imaged.

In a case where a radiation detector prepared by forming a conversion layer such as a scintillator on a flexible substrate having a photoelectric conversion element that converts light into an electrical signal is used, there are the following problems. That is, a flexible substrate such as polyimide (PI) has a lower thermal conductivity and a higher specific heat than a glass substrate. Therefore, in a manufacturing process of the radiation detector, there is a problem in that heat does not escape easily in a case where the heat is applied to the flexible substrate. Additionally, in a case where the radiographic imaging apparatus is actually used, there is a problem in that the heat is likely to stay on the flexible substrate and the temperature tends to rise.

When the temperature of the flexible substrate rises, thermal expansion occurs and warping of the flexible substrate occurs. As a result, there is a case where the sensor unit layer having the plurality of pixels that accumulates the electric charges generated depending on the light converted from the radiation is peeled off from the base material.

SUMMARY

A radiation detector of an aspect of the present disclosure includes a substrate including a sensor unit layer having a plurality of pixels for accumulating electric charges generated depending on light converted from radiation in a pixel region of a flexible base material; a conversion layer that is provided on a surface side of the base material provided with the pixel region to convert the radiation into light; and a fixing member that is provided closer to the substrate side than the conversion layer to fix the sensor unit layer to the base material.

DETAILED DESCRIPTION

Figure 1:
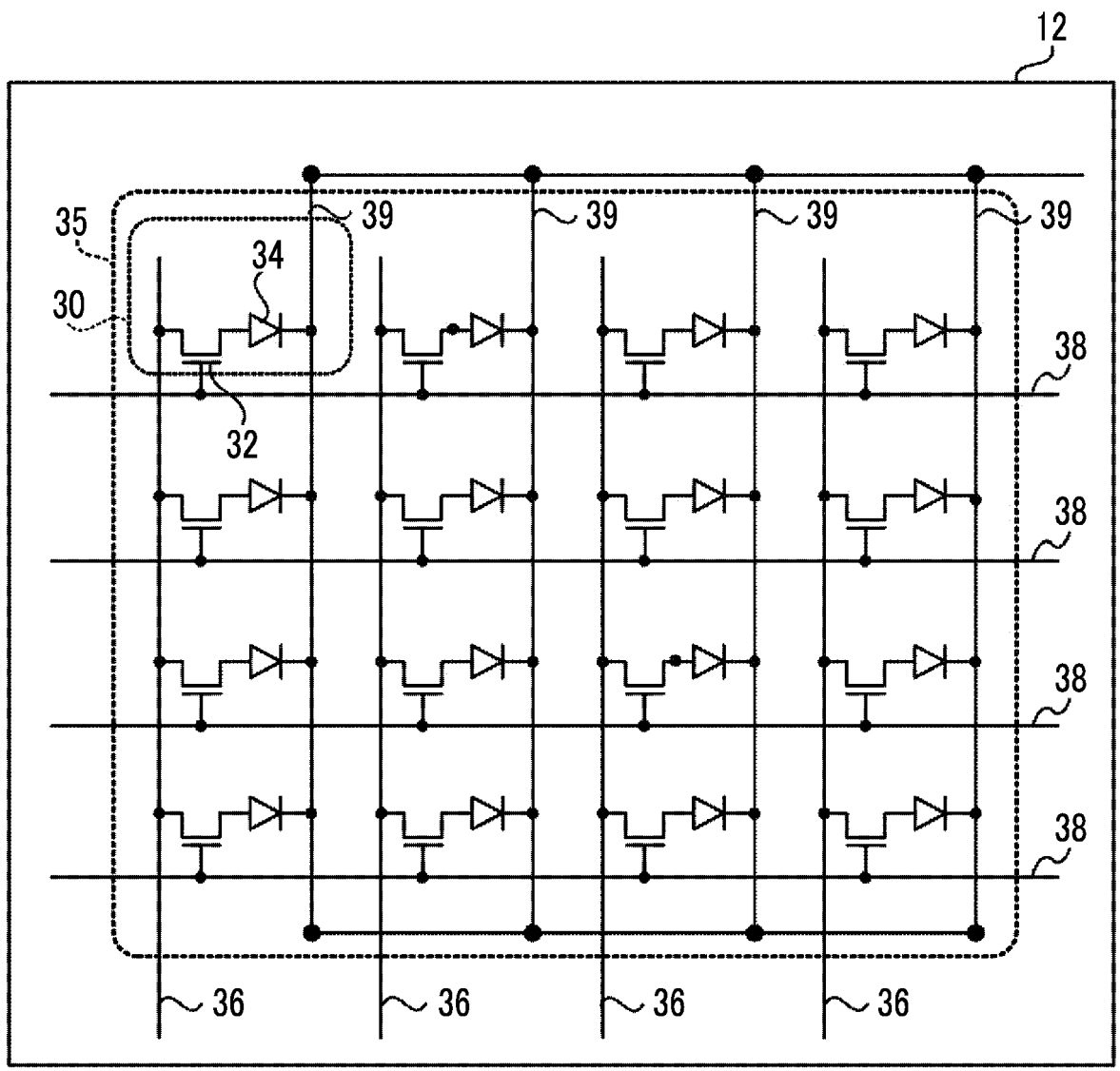
FIG. 1 is a configuration diagram illustrating an example of a configuration of a thin film transistor (TFT) substrate in a radiation detector according to a first embodiment.

Hereinafter, embodiments of the present invention will be described in detail with reference to the drawings. In addition, the present embodiment is not intended to be limited.

First Embodiment

A radiation detector of the present embodiment has a function of detecting radiation transmitted through a subject to output image information representing a radiographic image of the subject. The radiation detector of the present embodiment comprises a thin film transistor (TFT) substrate, and a conversion layer that converts radiation into light (refer to a TFT substrate 12 and a conversion layer 14 of a radiation detector 10 in FIG. 4).

An example of the configuration of the TFT substrate 12 in the radiation detector of the present embodiment will be described with reference to FIG. 1. The TFT substrate 12 of the present embodiment is a substrate in which a sensor unit layer 50 including a plurality of pixels 30 is formed in a pixel region 35 of a base material 11. The TFT substrate 12 of the present embodiment is an example of a substrate.

The base material 11 is made of resin and has flexibility. In addition, in the present embodiment, as an example, the base material 11 is formed as illustrated below.

First, a polyimide precursor solution is applied on the surface of an alkali-free glass substrate (Eagle 2000 manufactured by Corning Inc.) having a thickness of 0.7 mm by a bar coater such that the thickness of a film after thermosetting is 20 μm, and is dried at 130° C. for 10 minutes to form a polyimide precursor film.

Next, the temperature is raised from 100° C. to 360° C. for 2 hours under a nitrogen gas stream, and then heat treatment is performed at 360° C. for 2 hours to thermoset and imidize the polyimide precursor. Accordingly, a laminate having a glass substrate and a polyimide film layer can be obtained. The polyimide film of the obtained laminate can be easily peeled off from the glass substrate by hand. In addition, since the method of forming the base material 11 is also described in, for example, JP2014-218056A, further description thereof will be omitted.

The method of forming the base material 11 is not limited to this form, and the base material 11 may be formed by applying a resin containing a plastic such as polyimide onto a predetermined support body by an application method such as a spin coating method, an ink jet method, or a flexographic printing method. The base material obtained by applying an application type polyimide resin is hereinafter referred to as "application type polyimide base material". Additionally, as the base material 11, for example, a resin sheet containing a plastic such as polyimide may be used instead of the one obtained by applying the above resin.

The thickness of the base material 11 may be such that desired flexibility can be obtained depending on the hardness of the material, the size of the TFT substrate 12, and the like. For example, the base material 11 may have a thickness of 5 μm to 125 μm, and more preferably a thickness of 20 μm to 50 μm.

In addition, the base material 11 has such a property that the base material 11 can withstand the manufacture of the pixel 30, which will be described in detail below, and in the present embodiment, the base material 11 has such a property that the base material 11 can withstand the manufacture of an amorphous silicon TFT (a-Si TFT). As such a property of the base material 11, the coefficient of thermal expansion at 300° C. to 400° C. is preferably about the same as that of a silicon (Si) wafer (for example, ±5 ppm/K), and specifically, preferably 20 ppm/K or less. Additionally, as the percentage of thermal shrinkage of the base material 11, the percentage of thermal shrinkage in a machine direction (MD) at 400° C. in a state where the thickness is 25 μm is preferably 0.5% or less. Additionally, the modulus of elasticity of the base material 11 preferably does not have a transition point possessed by a general polyimide in a temperature range between 300° C. and 400° C., and the modulus of elasticity at 500° C. is preferably 1 GPa or more.

Figure 2:
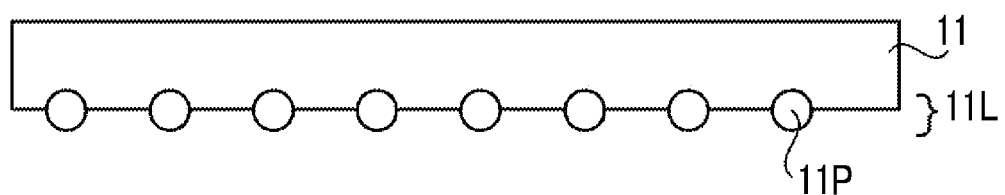
FIG. 2 is a cross-sectional view for explaining an example of a base material of the embodiment.

Additionally, in a case where a resin sheet is used as the base material 11 of the present embodiment, as illustrated in FIG. 2, it is preferable that a surface opposite to a side where the conversion layer 14 is provided have a fine particle layer 11L containing inorganic fine particles 11P of which the average particle diameter is 0.05 μm or more or 2.5 μm or less. An example of the resin sheet having such a property includes XENOMAX (registered trademark).

In addition, evaluation methods described in JP2010-076438A are applied as methods of measuring the thickness, the coefficient of thermal expansion, the modulus of elasticity, the average particle diameter, and the like that are described in the present embodiment. For example, a method of measuring the coefficient of thermal expansion is to measure the ratio of expansion and contraction in the machine direction (MD) and a transverse direction (TD) under the following conditions, measure the ratio of expansion and contraction and temperature at intervals of 10° C., such as 90° C. to 100° C., 100° C. to 110° C., and . . . , perform this measurement up to 400° C., and convert the coefficient of thermal expansion (ppm/° C.) derived as an average value of all measured values from 100° C. to 350° C. into a coefficient of thermal expansion in units of ppm/K. As the measurement conditions of the coefficient of thermal expansion, the TMA4000S apparatus manufactured by MAC SCIENCE CO., LTD. was used, the sample length was 10 mm, the sample width was 2 mm, the initial load was 34.5 g/mm$^2$, the temperature rising start temperature was 25° C., the temperature rising end temperature was 400° C., the temperature rising rate was 5° C./min, and the atmosphere was argon.

Each of the pixels 30 includes a sensor unit 34 that generates and accumulates electric charges in accordance with the light converted by the conversion layer 14, and a switching element 32 that reads out the electric charges accumulated by the sensor unit 34. In the present embodiment, as an example, a thin film transistor (TFT) is used as the switching element 32. For that reason, in the following description, the switching element 32 is referred to as a "TFT 32".

The plurality of pixels 30 is two-dimensionally disposed in one direction (a scanning wiring direction corresponding to a transverse direction of FIG. 1, hereinafter referred to as a "row direction"), and a direction (a signal wiring direction corresponding to a longitudinal direction of FIG. 1, hereinafter referred as a "column direction") intersecting the row direction in the pixel region 35 of the TFT substrate 12. Although an array of the pixels 30 is illustrated in a simplified manner in FIG. 1, for example, 1024×1024 pixels 30 are disposed in the row direction and the column direction.

Additionally, a plurality of scanning wiring lines 38 for controlling switching states (ON and OFF) of the TFTs 32, and a plurality of signal wiring lines 36, which is provided for respective columns of the pixels 30 and from which electric charges accumulated in the sensor units 34 are read, are provided in a mutually intersecting manner in the radiation detector 10. The plurality of scanning wiring lines 38 is respectively connected to a drive unit 103 (refer to FIG. 6) outside the radiation detector 10 via a connection region 43 (refer to FIGS. 4 and 6), respectively, provided in the TFT substrate 12, and thereby, control signals, which are output from the drive unit 103 to control the switching states of the TFTs 32, flow to the plurality of scanning wiring lines 38, respectively. Additionally, the plurality of signal wiring lines 36 is respectively connected to a signal processing unit 104 (refer to FIG. 6) outside the radiation detector 10 via the connection region 43 (refer to FIGS. 4 and 6), respectively, provided in the TFT substrate 12, and thereby, electric charges read from the respective pixels 30 is output to the signal processing unit 104.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by connecting the common wiring lines 39 to the bias power source outside the radiation detector 10 via pads provided in the TFT substrate 12.

Figure 3:
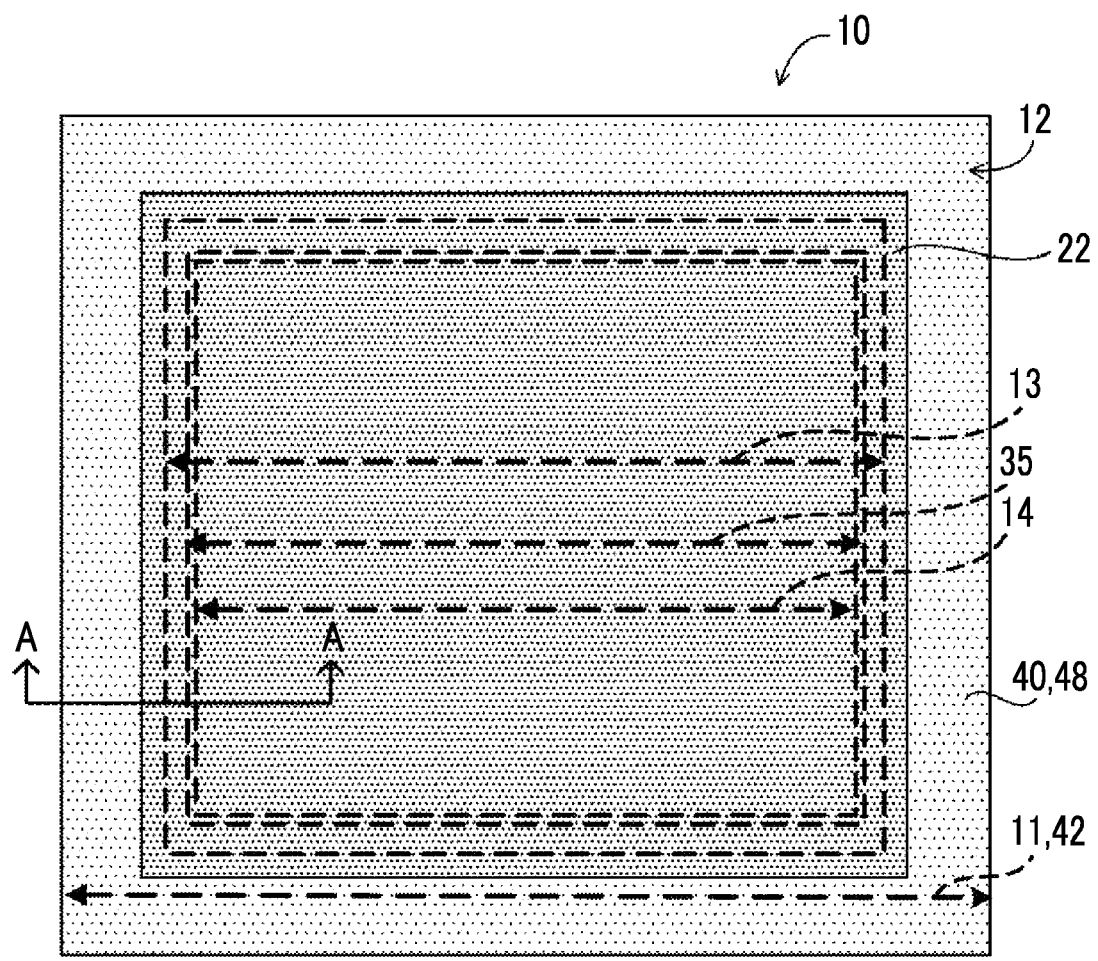
FIG. 3 is a plan view of an example of the radiation detector of the first embodiment as seen from the side on which a conversion layer is provided.
Figure 4:
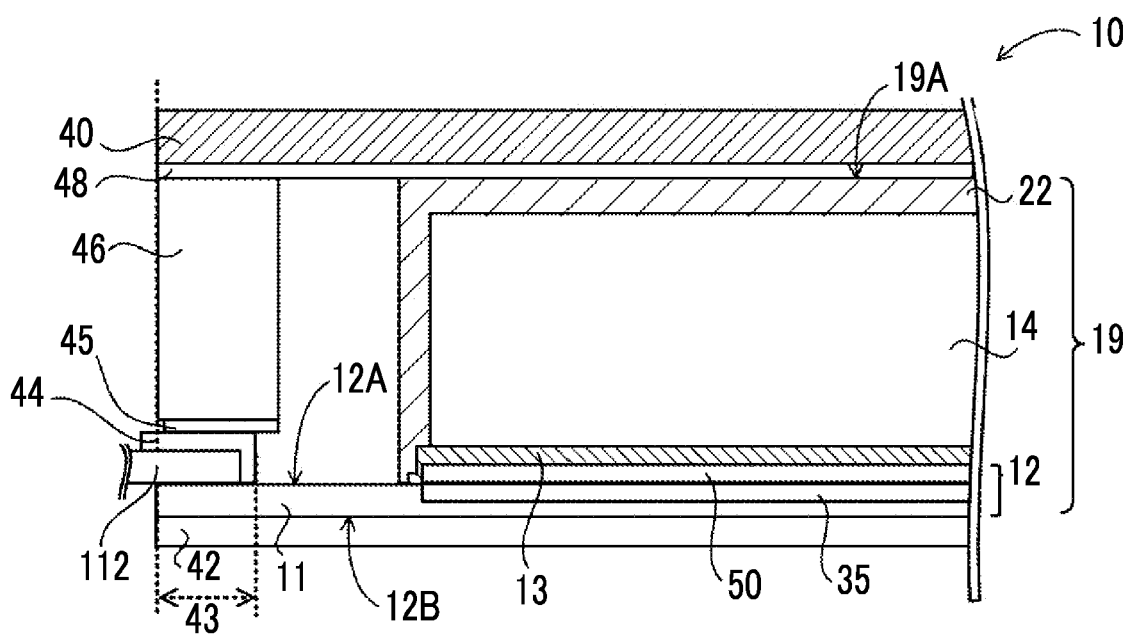
FIG. 4 is a cross-sectional view taken along line A-A of the radiation detector illustrated in FIG. 3.
Figure 5:
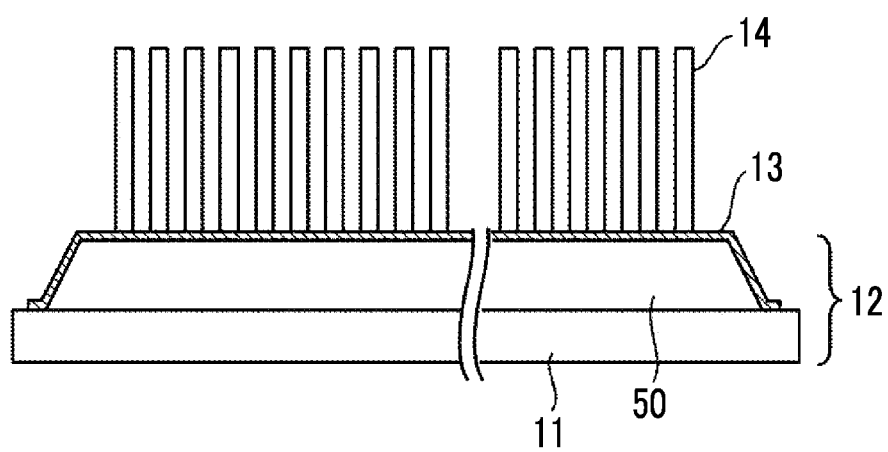
FIG. 5 is a cross-sectional view illustrating the configuration of main parts of the radiation detector illustrated in FIG. 3.

In the radiation detector 10 of the present embodiment, the conversion layer 14 is formed on the TFT substrate 12. FIG. 3 is a plan view of the radiation detector 10 of the present embodiment as seen from a side on which the conversion layer 14 is formed. Additionally, FIG. 4 is a cross-sectional view taken along line A-A of the radiation detector 10 in FIG. 3. Moreover, FIG. 5 is a cross-sectional view illustrating the configuration of main parts of the radiation detector illustrated in FIG. 3. In addition, in the following description, the term "on" in the structure of the radiation detector 10 means "on" in a positional relationship with reference to the TFT substrate 12 side. For example, the conversion layer 14 is provided on the TFT substrate 12.

As illustrated in FIGS. 3 and 4, the conversion layer 14 of the present embodiment is provided on a partial region including the pixel region 35 on a first surface 12A of the TFT substrate 12. In this way, the conversion layer 14 of the present embodiment is not provided on the region of an outer peripheral part on the first surface 12A of the TFT substrate 12. The first surface 12A of the present embodiment is an example of a surface provided with the pixel region of the present disclosure.

In the present embodiment, a scintillator including CsI (cesium iodide) is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:Tl is 565 nm.

In the radiation detector 10 of the present embodiment, the conversion layer 14 is formed on the TFT substrate 12 as strip-shaped columnar crystals by vapor-phase deposition methods, such as a vacuum vapor deposition method, a sputtering method, and a chemical vapor deposition (CVD) method. For example, in a case where CsI:Tl is used as the conversion layer 14, a vacuum vapor deposition method is used as a method of forming the conversion layer 14. In the vacuum vapor deposition method, CsI:Tl is heated and gasified by heating means, such as a resistance heating-type crucible in an environment with the vacuum degree of 0.01 Pa to 10 Pa, and CsI:Tl is deposited on the TFT substrate 12 with the temperature of the TFT substrate 12 as the room temperature (20° C.) to 300° C. As the thickness of the conversion layer 14, 100 μm to 800 μm is preferable.

In the radiation detector 10 according to the present embodiment, in order to reduce the weight, a resin containing a plastic such as polyimide is used for the base material 11 instead of glass. For this reason, in a case where the temperature of the radiation detector 10 has risen, compared to a case where glass is used, the thermal expansion of the TFT substrate 12 becomes larger and large warpage occurs in the TFT substrate 12. As a result, there is a possibility that the sensor unit layer 50 is peeled off from the base material 11. Particularly, this problem is remarkable in a case where the base material 11 is an application type polyimide base material. In this case, the coefficient of thermal expansion is about 10 times that of a base material using glass. As a result, the possibility that the sensor unit layer 50 is peeled off from the base material 11 increases.

Thus, in the present embodiment, as illustrated in FIGS. 4 and 5 as an example, a fixing layer 13 for fixing the sensor unit layer 50 to the base material 11 is provided between the TFT substrate 12 and the conversion layer 14. The fixing layer 13 further has a function of buffering a difference between the coefficient of thermal expansion of the conversion layer 14 and the coefficient of thermal expansion of the base material 11. The greater the difference between the coefficient of thermal expansion of the conversion layer 14 and the coefficient of thermal expansion of the base material 11, the greater the significance of providing the fixing layer 13. For example, in a case where XENOMAX (registered trademark) is used for the base material 11, the difference from the coefficient of thermal expansion of the conversion layer 14 is larger than that of other materials. Therefore, the significance of providing the fixing layer 13 as in the radiation detector 10 illustrated in FIGS. 4 and 5 is great.

In the present embodiment, the fixing layer 13 contains the same material as the base material 11. Specifically, in a case where the application type polyimide base material is used as the base material 11, one obtained by applying the application type polyimide resin is used as the fixing layer 13. In this way, in the present embodiment, one containing the same material as the base material 11 is used as the fixing layer 13. Therefore, the difference in the coefficient of thermal expansion between the fixing layer 13 and the base material 11 can be reduced. As a result, the occurrence of warpage of the TFT substrate 12 can be suppressed. However, the present invention is not limited to this form, and a Parylene (registered trademark) film may be used as the fixing layer 13. The fixing layer 13 of the present embodiment is an example of a fixing member.

In the present embodiment, the fixing layer 13 fixes the sensor unit layer 50 to the base material 11 at its end part. More specifically, as illustrated in FIGS. 4 and 5, in the present embodiment, the fixing layer 13 covers a region ranging formed from the entire surface of the sensor unit layer 50 on the conversion layer 14 side via an end surface of the sensor unit layer 50 to a portion of the surface of the base material 11 on the sensor unit layer 50 side, thereby fixing the sensor unit layer 50 to the base material 11.

In addition, in the examples illustrated in FIGS. 4 and 5, the end part of the fixing layer 13 on the base material 11 side covers only a portion of the surface of the base material 11 on the sensor unit layer 50 side. However, the present invention is not limited to this form, and the fixing layer 13 may cover the entire upper surface of the base material 11 except for the region of the sensor unit layer 50.

In a case where polyimide is used as the fixing layer 13, the fixing layer 13 is formed by applying the polyimide on the sensor unit layer 50 by an application method such as a spin coating method, an ink jet method, or a flexographic printing method. In this case, since the polyimide is colored, it is preferable not to make the polyimide too thick in order to transmit the light generated in the conversion layer 14 and absorb the light with a photodiode, and the thickness of the fixing layer 13 is preferably about 0.05 to 0.2 μm and more preferably about 0.1 μm.

In contrast, in a case where the Parylene (registered trademark) film is used as the fixing layer 13, the fixing layer 13 is formed by applying the Parylene (registered trademark) on the sensor unit layer 50 by a vacuum film formation method. Specifically, the TFT substrate 12 formed up to the sensor unit layer 50 is put into a vacuum chamber, a Parylene (registered trademark) raw material is heated and evaporated at a predetermined vacuum degree, and a Parylene (registered trademark) film is formed on the TFT substrate 12. In this case, the thickness of the fixing layer 13 is preferably about 0.5 to 10 µm. In addition, a region where the Parylene (registered trademark) film is not desired to be formed may be appropriately masked.

In the present embodiment, the ratio of the coefficient of thermal expansion $CTE_{flex}$ (CTE: Coefficient of Thermal Expansion) of the base material 11 and the coefficient of thermal expansion $CTE_{sur}$ of the fixing layer 13 (hereinafter referred to as "CTE ratio") is a value in a range shown in the following Formula (1).

$$0.5 \leq \frac{CTE_{sur}}{CTE_{flex}} \leq 4 \qquad (1)$$

In a case where the application type polyimide resin is used as the fixing layer 13, the coefficient of thermal expansion CTE of the polyimide is in a range of about 18 to 38 PPM/degree. Therefore, the CTE ratio is in a range of about 0.5 or more and 2 or less.

In contrast, in a case where the Parylene (registered trademark) is used as the fixing layer 13, the coefficient of thermal expansion CTE of the Parylene (registered trademark) is in a range of about 35 to 69 PPM/degree. Therefore, the CTE ratio is in a range of about 0.5 or more and 4 or less.

As illustrated in FIG. 4, the conversion layer 14 is covered with a protective layer 22. The protective layer 22 has a function of protecting the conversion layer 14 from moisture, such as humidity. Examples of the material of the protective layer 22 include organic films, and specifically single films or laminated films made of polyethylene terephthalate (PET), polyphenylene sulfide (PPS), biaxially stretched polypropylene film (OPP: Oriented PolyPropylene), polyethylene naphthalate (PEN), and the like. Additionally, as the protective layer 22, an ALPET (registered trademark) sheet obtained by laminating aluminum, for example by causing aluminum foil to adhere to an insulating sheet (film), such as PET may be used. In the present embodiment, the fixing layer 13 is made of a material different from that of the protective layer 22.

A reinforcing substrate 40 is provided by a pressure sensitive adhesive layer 48 on a first surface 19A, which is the surface, on the conversion layer 14 side, of a laminate 19 in which the TFT substrate 12, the fixing layer 13, the conversion layer 14, and the protective layer 22 are laminated.

The reinforcing substrate 40 has a higher stiffness than the base material 11, and a dimensional change (deformation) due to a force applied in a direction perpendicular to the surface facing the conversion layer 14 is smaller than a dimensional change due to a force applied perpendicular to the first surface 12A of the TFT substrate 12. Additionally, the thickness of the reinforcing substrate 40 of the present embodiment is larger than the thickness of the base material 11. In addition, the stiffness referred to herein means the difficulty of bending the reinforcing substrate 40 and the base material 11 including the thickness of the reinforcing substrate 40 and the base material 11, and means that the higher the stiffness, the more difficult it is to bend.

Additionally, the reinforcing substrate 40 of the present embodiment is a substrate containing a material having a yield point. In addition, in the present embodiment, the "yield point" refers to a phenomenon in which the stress once falls sharply in a case where the material is pulled, and a point indicating a yield on a curve showing a relationship between the stress and the strain. Resins having the yield point generally include resins that are hard and sticky, and resins that are soft and sticky and have medium strength. Examples of the hard and sticky resins include polycarbonate (PC) and polyamide. Additionally, examples of the soft, sticky, and medium-strength resins include high-density polyethylene and polypropylene.

Additionally, the reinforcing substrate 40 of the present embodiment preferably has a bending elastic modulus of 1000 MPa or more and 2500 MPa or less. The method for measuring the bending elastic modulus is based on, for example, JIS standard. As the bending elastic modulus becomes lower, the reinforcing substrate 40 should be thickened for stiffness. For that reason, from the viewpoint of suppressing the thickness, the reinforcing substrate 40 preferably has a bending elastic modulus of 2000 MPa or more and 2500 MPa or less.

Additionally, the coefficient of thermal expansion of the reinforcing substrate 40 of the present embodiment is preferably closer to the coefficient of thermal expansion of the material of the conversion layer 14, and more preferably the ratio of the coefficient of thermal expansion of the reinforcing substrate 40 to the coefficient of thermal expansion of the conversion layer 14 is preferably 0.5 or more and 2 or less. For example, in a case the conversion layer 14 is made of CsI:Tl as a material, the coefficient of thermal expansion is 50 ppm/K. In this case, materials for the reinforcing substrate 40 include polyvinyl chloride (PVC) having a coefficient of thermal expansion of 60 ppm/K to 80 ppm/K, acrylic having a coefficient of thermal expansion of 70 ppm/K to 80 ppm/K, and a coefficient of thermal expansion of 65 to 70 ppm/K. PET, a PC having a coefficient of thermal expansion of 65 ppm/K, and Teflon (registered trademark) having a coefficient of thermal expansion of 45 ppm/K to 70 ppm/K. Moreover, in consideration of the above-described bending elastic modulus, the material of the reinforcing substrate 40 is more preferably a material containing at least one of PET or PC.

In addition, the reinforcing substrate 40 may be further reinforced by covering the reinforcing substrate 40 with an additional reinforcing substrate, and the additional reinforcing substrate may be, for example, a rigid plate such as a carbon plate. Even in a case where the entire surface of the conversion layer 14 is covered with the additional reinforcing substrate, in a case where the material of the additional reinforcing substrate is carbon or the like having a small amount of X-ray absorption, X-ray loss can be suppressed in any of irradiation side sampling type (ISS:) and a penetration side sampling type (PSS). Here, the X-ray loss means that the emitted X-rays are absorbed by the additional reinforcing substrate, and thereby, the X-rays reaching the conversion layer 14 are reduced. The additional reinforcing substrate has a bending elastic modulus larger than that of the reinforcing substrate 40.

The bending elastic modulus of the additional reinforcing member is preferably, for example, 8,000 MPa or more. Additionally, an upper limit of the bending elastic modulus of the additional reinforcing member is preferably 60,000 MPa or less. In addition, the bending elastic modulus of carbon is about 8,000 MPa to 50,000 MPa, and carbon is suitable as the additional reinforcing member from the viewpoint of the bending elastic modulus.

As illustrated in FIGS. 3 and 4, the reinforcing substrate 40 of the present embodiment is provided in a region wider than the region of the first surface 12A of the TFT substrate 12 in which the conversion layer 14 is provided. For that reason, as illustrated in FIGS. 3 and 4, the end part of the reinforcing substrate 40 protrudes outward from an outer peripheral part of the conversion layer 14 (the outer peripheral part side of the TFT substrate 12).

Figure 6:
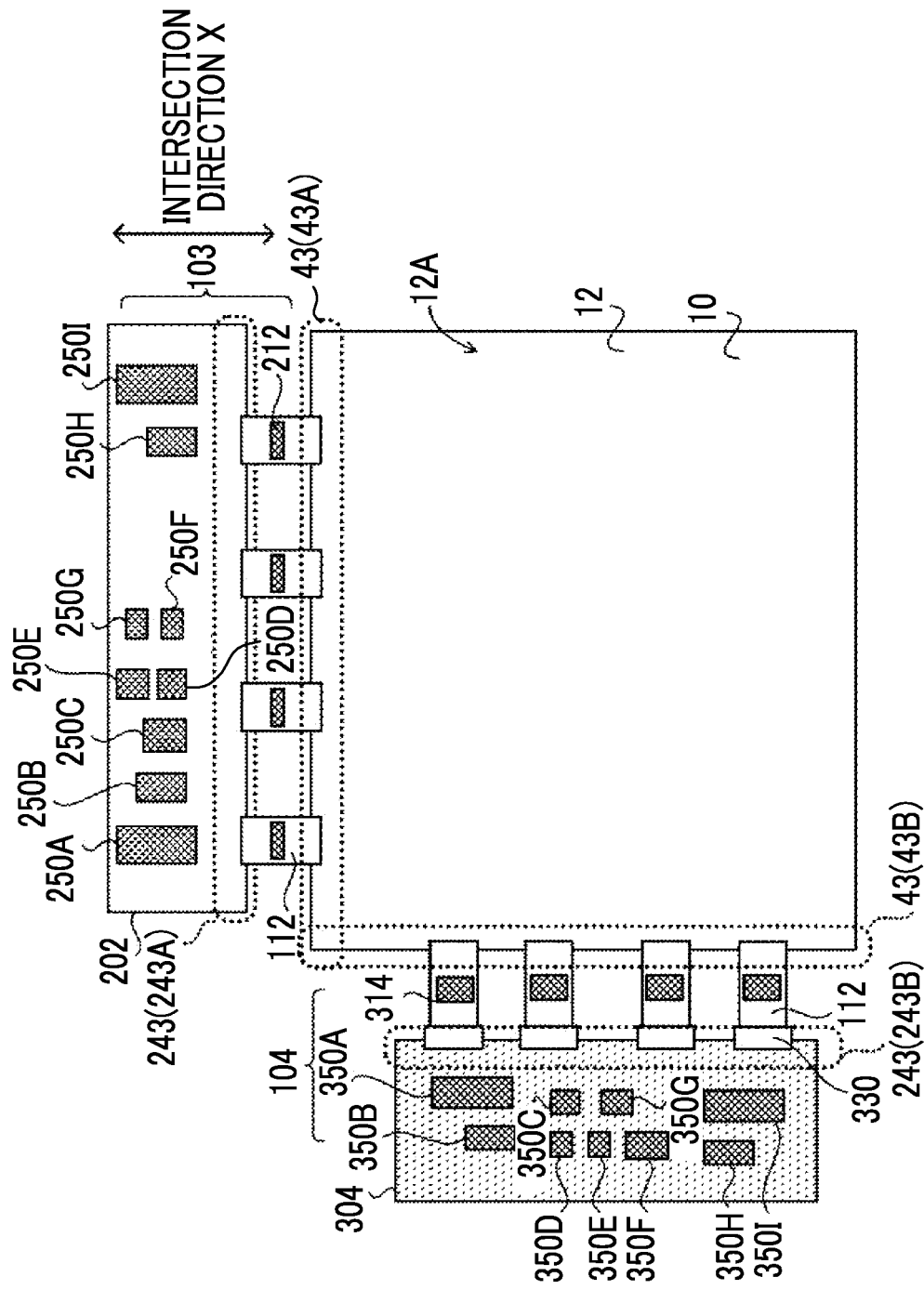
FIG. 6 is a plan view of the example of the radiation detector of the first embodiment as seen from a first surface side of a TFT substrate.

As illustrated in FIG. 4, the connection region 43 is provided on an outer peripheral part of the TFT substrate 12. A flexible cable 112, which will be described in detail below, is connected to the connection region 43. The flexible cable 112 is connected to any one of the drive unit 103 and the signal processing unit 104 (refer to FIG. 6 for both). The drive unit 103 and the signal processing unit 104 of the present embodiment are examples of a circuit unit of the present disclosure. FIG. 6 illustrates a plan view of the TFT substrate 12 as viewed from the first surface 12A side as an example of a state in which the drive unit 103 and the signal processing unit 104 are connected to the radiation detector 10 of the present embodiment.

As in the example illustrated in FIG. 6, the flexible cable 112 is electrically connected to the connection region 43 of the TFT substrate 12. In addition, in the present embodiment, the connection related to a component referred to as a "cable" including the flexible cable 112 means an electrical connection unless otherwise specified. The flexible cable 112 includes a signal line that is a conductor, and the signal line is connected to the connection region 43, and thereby electrically connected thereto. The flexible cable 112 of the present embodiment is an example of a flexible wiring line.

One end of each of a plurality of (four in FIG. 6) flexible cables 112 is thermocompression-bonded to the connection region 43 (43A) of the TFT substrate 12. The flexible cable 112 has a function of connecting the drive unit 103 and the scanning wiring lines 38 (refer to FIG. 1). A plurality of signal lines included in the flexible cable 112 are connected to the scanning wiring lines 38 (refer to FIG. 1) of the TFT substrate 12 via the connection region 43.

On the other hand, the other end of the flexible cable 112 is thermocompression-bonded to the connection region 243 (243A) provided in an outer peripheral region of the driving substrate 202. The plurality of signal lines included in the flexible cable 112 are connected to drive components 250 that are a circuit, an element, and the like mounted on the driving substrate 202 via the connection region 243.

FIG. 6 illustrates, as an example, a state in which nine drive components 250 (250A to 250I) are mounted on the driving substrate 202. As illustrated in FIG. 6, the drive components 250 of the present embodiment are disposed in an intersection direction X that is a direction intersecting a bending direction Y that is a direction along a side corresponding to the connection region 43 (43A) of the TFT substrate 12.

The driving substrate 202 of the present embodiment is a flexible PCB (printed circuit board) substrate, that is, a flexible substrate. The drive components 250 mounted on the driving substrate 202 is a component mainly used for processing digital signals (hereinafter, referred to as "digital components"). Examples of the drive components 250 include a digital buffer, a bypass capacitor, a pull-up/pull-down resistor, a damping resistor, an electro magnetic compatibility (EMC) countermeasure chip component, and the like. In addition, the driving substrate 202 may not necessarily be a flexible substrate, and may be a non-flexible rigid substrate, which will be described below.

The digital components tend to have a relatively smaller area (size) than analog components, which will be described below. Additionally, digital components tend to be less susceptible to electrical interference, for example, noise than the analog components. For that reason, in the present embodiment, in a case where the TFT substrate 12 is bent, the side of a substrate that is bent with the bending of the TFT substrate 12 is the driving substrate 202 on which the drive components 250 are mounted.

Additionally, a drive circuit unit 212 is mounted on the flexible cable 112 connected to the driving substrate 202. The drive circuit unit 212 is connected to the plurality of signal lines included in the flexible cable 112.

In the present embodiment, the drive unit 103 is realized by the drive components 250 mounted on the driving substrate 202, and the drive circuit unit 212. The drive circuit unit 212 is an integrated circuit (IC) including a circuit different from the drive components 250 mounted on the driving substrate 202 among various circuits and elements that realize the drive unit 103.

In this way, in the radiation detector 10 of the present embodiment, the TFT substrate 12 and the driving substrate 202 are electrically connected to each other by the flexible cable 112, and thereby, the drive unit 103 and each of the scanning wiring lines 38 are connected to each other.

Meanwhile, one end of each of a plurality of (four in FIG. 6) flexible cables 112 is thermocompression-bonded to the connection region 43 (43B) of the TFT substrate 12. The plurality of signal lines included in the flexible cable 112 are connected to the signal wiring lines 36 (refer to FIG. 1) via the connection region 43. The flexible cable 112 has a function of connecting the signal processing unit 104 and the signal wiring lines 36 (refer to FIG. 1) to each other.

Meanwhile, the other end of the flexible cable 112 is electrically connected to a connector 330 provided in the connection region 243 (243B) of a signal processing substrate 304. The plurality of signal lines included in the flexible cable 112 are connected to signal processing components 350 that are a circuit, an element, and the like mounted on the signal processing substrate 304 via the connector 330. For example, examples of the connector 330 include a zero insertion force (ZIF) structure connector and a Non-ZIF structure connector. FIG. 6 illustrates, as an example, a state in which nine signal processing components 350 (350A to 350I) are mounted on the signal processing substrate 304. As illustrated in FIG. 6, the signal processing components 350 of the present embodiment are disposed in the intersection direction X that is the direction along the connection region 43 (43B) of the TFT substrate 12.

In addition, the signal processing substrate 304 of the present embodiment is a non-flexible PCB substrate, that is, a rigid substrate. For that reason, the thickness of the signal processing substrate 304 is larger than that of the driving substrate 202. Additionally, the signal processing substrate 304 has a higher stiffness than the driving substrate 202.

The signal processing components 350 mounted on the signal processing substrate 304 are components mainly used for processing analog signals (hereinafter, referred to as "analog components"). Examples of the signal processing components 350 include an operational amplifier, an analog-to-digital converter (ADC), a digital-to-analog converter (DAC), a power supply IC, and the like. Additionally, the signal processing components 350 of the present embodiment also include a coil around a power supply having a relatively large component size and a large-capacity smoothing capacitor.

As described above, the analog components tend to have a relatively larger area (size) than the digital components. Additionally, the analog components tend to be more susceptible to electrical interference, for example noise, than the digital components. For that reason, in the present embodiment, even in a case where the TFT substrate 12 is bent, the side of the substrate that is not bent (is not affected by the bending) is the signal processing substrate 304 on which the signal processing components 350 are mounted.

Additionally, a signal processing circuit unit 314 is mounted on the flexible cable 112 connected to the signal processing substrate 304. The signal processing circuit unit 314 is connected to the plurality of signal lines included in the flexible cable 112.

In the present embodiment, the signal processing unit 104 is realized by the signal processing components 350 mounted on the signal processing substrate 304, and the signal processing circuit unit 314. The signal processing circuit unit 314 is an IC including a circuit different from the signal processing components 350 mounted on the signal processing substrate 304 among various circuits and elements that realize the signal processing unit 104.

In this way, in the radiation detector 10 of the present embodiment, the TFT substrate 12 and the signal processing substrate 304 are electrically connected to each other by the flexible cable 112, and thereby the signal processing unit 104 and each of the signal wiring lines 36 are connected to each other.

Additionally, as in the example illustrated in FIG. 4, in the radiation detector 10 of the present embodiment, a spacer 46 that seals the side surfaces of the conversion layer 14 is provided with the flexible cable 112, a moistureproof agent 44, and a pressure sensitive adhesive layer 45 interposed between the reinforcing substrate 40 and the first surface 12A of the TFT substrate 12.

The method of providing the spacer 46 is not particularly limited, and for example, the spacer 46 may be provided between the TFT substrate 12 and the reinforcing substrate 40 by bonding the spacer 46 to the pressure sensitive adhesive layer 48 of the end part of the reinforcing substrate 40 and bonding the reinforcing substrate 40 in a state where the spacer 46 is provided, to the TFT substrate 12 in a state where the laminate 19, the flexible cable 112, the moistureproof agent 44, and the pressure sensitive adhesive layer 45 are provided. In addition, the width of the spacer 46 (the width thereof in the direction intersecting a lamination direction of the laminate 19) is not limited to the example illustrated in FIG. 4. For example, the width of the spacer 46 may be expanded to a position closer to the conversion layer 14 than the example illustrated in FIG. 4. Additionally, the spacer 46 may be formed by caulking a resin, ceramic, or the like on the first surface 12A of the TFT substrate 12.

Additionally, a protective film 42 having a function of protecting from moisture such as humidity is provided on a second surface 12B of the TFT substrate 12 of the present embodiment. Examples of the material of the protective film 42 include the same materials as the protective layer 22.

An example of a method of manufacturing the radiation detector 10 of the present embodiment includes the following method. An example of the method of manufacturing the radiation detector 10 of the present embodiment will be described with reference to FIGS. 4, 7, and 8. In addition, FIG. 8 illustrates a case where the number of flexible cables 112 connected to the driving substrate 202 is six.

One in a state in which the pressure sensitive adhesive layer 48 is applied on the reinforcing substrate 40 having a desired size adapted to the size of the radiation detector 10 and the spacer 46 is provided on the pressure sensitive adhesive layer 48 is prepared in advance.

Figure 7:
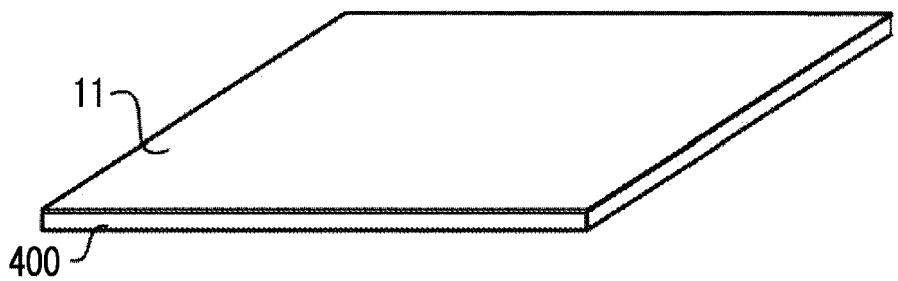
FIG. 7 is an explanatory view illustrating an example of a method of manufacturing the radiation detector of the first embodiment.
Figure 8:
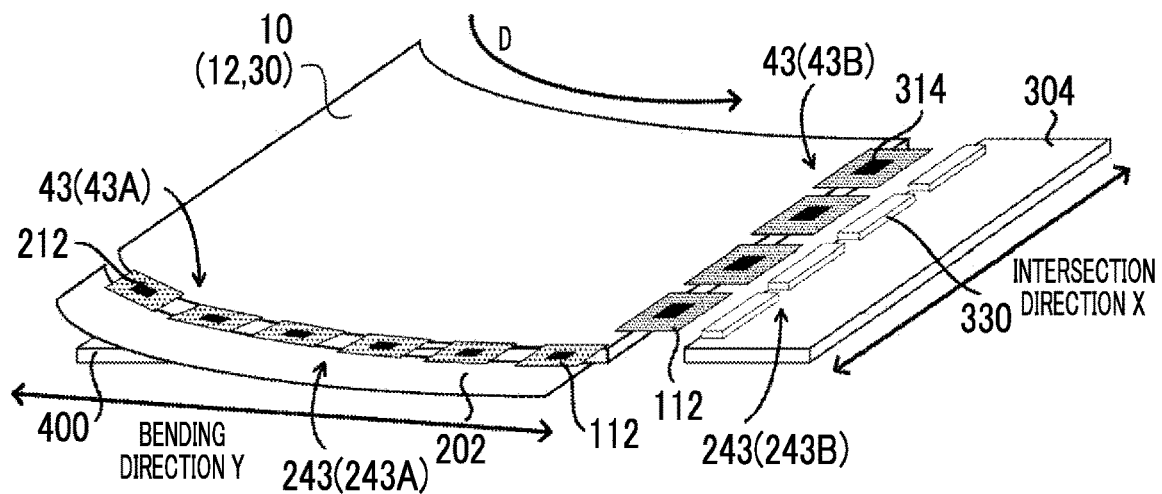
FIG. 8 is an explanatory view illustrating an example of a method of manufacturing the radiation detector of the first embodiment.

Meanwhile, as illustrated in FIG. 7, the base material 11 is formed on a support body 400, such as a glass substrate which is thicker than the base material 11, via a peeling layer. The surface of the base material 11 corresponding to the second surface 12B of the TFT substrate 12 is in contact with the peeling layer.

Moreover, as illustrated in FIG. 4, the sensor unit layer 50 including the plurality of pixels 30 is formed in the pixel region 35 of the base material 11. In addition, in the present embodiment, as an example, the sensor unit layer 50 is formed in the pixel region 35 of the base material 11 via an undercoat layer using SiN or the like.

Moreover, the conversion layer 14 is formed on the sensor unit layer 50. In the present embodiment, first, the fixing layer 13 is formed in the region ranging from the entire surface of the sensor unit layer 50 on the conversion layer 14 side in the first surface 12A of the TFT substrate 12 via the end surface of the sensor unit layer 50 to a portion of the base material 11 on the sensor unit layer 50 side. Thereafter, the CsI conversion layer 14 is formed as a columnar crystal directly on the TFT substrate 12 and more specifically on the fixing layer 13 by a vapor-phase deposition method such as a vacuum vapor deposition method, a sputtering method, and a chemical vapor deposition (CVD) method. In this case, the side of the conversion layer 14 in contact with the pixels 30 is a growth direction base point side of the columnar crystal.

In addition, in a case where the CsI conversion layer 14 is provided directly on the fixing layer 13 by the vapor-phase deposition method in this way, for example, a reflective layer having a function of reflecting the light converted in the conversion layer 14 may be provided on the surface of the conversion layer 14 opposite to the side in contact with the fixing layer 13. The reflective layer may be provided directly on the conversion layer 14 or may be provided via an adhesion layer or the like. As a material of the reflective layer, it is preferable to use an organic material, and it is preferable to use, for example, at least one of white PET, $TiO_2$, $Al_2O_3$, foamed white PET, a polyester-based high-reflection sheet, specular reflection aluminum, or the like. Particularly, it is preferable to use the white PET as the material from a viewpoint of reflectance. In addition, the polyester-based high-reflection sheet is a sheet (film) having a multilayer structure in which a plurality of thin polyester sheets is laminated.

Additionally, in a case where a CsI scintillator is used as the conversion layer 14, the conversion layer 14 can be formed on the TFT substrate 12 (fixing layer 13) by a method different from that of the present embodiment. For example, the conversion layer 14 may be formed on the TFT substrate 12 (fixing layer 13) by preparing one in which CsI is vapor-deposited on an aluminum plate or the like by a vapor-phase deposition method and bonding a side of the CsI, which is not in contact with the aluminum plate, and the TFT substrate 12 (fixing layer 13) to each other with a pressure sensitive adhesive sheet or the like. In this case, it is preferable that one in which the entire conversion layer 14 also including the aluminum plate is covered with a protective film is bonded to the TFT substrate 12 (fixing layer 13). In addition, in this case, the side of the conversion layer 14 in contact with the fixing layer 13 is a distal end side in the growth direction of the columnar crystal.

Additionally, unlike the radiation detector 10 of the present embodiment, GOS ($Gd_2O_2S:Tb$) or the like may be used as the conversion layer 14 instead of CsI. In this case, for example, the conversion layer 14 can be formed on the TFT substrate 12 by preparing one in which a sheet having GOS dispersed in a binder such as resin is bonded to a support body formed of white PET or the like with a pressure sensitive adhesive layer or the like, and bonding a side o the GOS on which the support body is not bonded, and the TFT substrate 12 (fixing layer 13) to each other with the pressure sensitive adhesive sheet or the like. In addition, the conversion efficiency from radiation to visible light is higher in a case where CsI is used for the conversion layer 14 than in a case where GOS is used for the conversion layer 14.

Moreover, the flexible cable 112 is thermocompression-bonded to the connection regions 43 (43A and 43B) of the TFT substrate 12, and the plurality of signal lines included in the flexible cable 112 and the connection regions 43 (43A and 43B) of the TFT substrate 12 are electrically connected to each other.

Moreover, the flexible cable 112 is thermocompression-bonded to the connection region 243 (243A) of the driving substrate 202, and the plurality of signal lines included in the flexible cable 112 and the drive components 250 mounted on the driving substrate 202 are electrically connected to each other.

Then, the reinforcing substrate 40 provided with the spacer 46, which has been prepared in advance, is bonded to the TFT substrate 12 on which the conversion layer 14 is formed and the flexible cable 112 is connected, thereby sealing the conversion layer 14. In addition, in a case where the above bonding is performed, the bonding is performed under the atmospheric pressure or under reduced pressure (under vacuum). However, in order to suppress entry of air or the like while being bonded to each other, it is preferable to perform the bonding under reduced pressure.

Thereafter, the radiation detector 10 is peeled off from the support body 400 as illustrated in FIG. 8. In a case where the peeling is performed by mechanical peeling, in the example illustrated in FIG. 8, a side of the TFT substrate 12 facing a side to which the flexible cable 112 is connected is used as a starting point of the peeling, and the TFT substrate 12 is peeled off in a direction of arrow D illustrated in FIG. 8 from the support body 400 gradually toward the side to which the flexible cable 112 is connected from the side serving as the starting point. Accordingly, the mechanical peeling is performed, and the radiation detector 10 in a state where the flexible cable 112 is connected is obtained.

In addition, the side serving as the starting point of the peeling is preferably a side that intersects the longest side in a case where the TFT substrate 12 is viewed in a plan view. That is, a side extending in the bending direction Y in which bending occurs due to the peeling is preferably the longest side. In the present embodiment, a side to which the driving substrate 202 is connected by the flexible cable 112 is longer than a side to which the signal processing substrate 304 is connected by the flexible cable 112. For that reason, the starting point of the peeling is used as a side facing a side where the connection region 43 (43B) is provided.

In the present embodiment, after the TFT substrate 12 is further peeled off from the support body 400, the flexible cable 112 of the radiation detector 10 and the connector 330 of the signal processing substrate 304 are electrically connected to each other. In this way, in the present embodiment, the radiation detector 10 illustrated as an example in FIGS. 3 to 5 is manufactured.

In addition, the method of manufacturing the radiation detector 10 is not limited to the present embodiment, and mechanical peeling may be performed after the flexible cable 112 of the radiation detector 10 and the connector 330 of the signal processing substrate 304 are electrically connected to each other.

In performing the mechanical peeling, in the radiographic imaging apparatus 1 of the present embodiment (refer to FIG. 15 described below), as illustrated in FIG. 8, the driving substrate 202 is a flexible substrate. Therefore, the driving substrate 202 is also bent depending on the bending of the TFT substrate 12.

Here, in a case where the TFT substrate 12 is peeled from the support body 400, the TFT substrate 12 is easily bent because the base material 11 has flexibility. In a case where the TFT substrate 12 is greatly bent, the conversion layer 14 is also largely bent. As a result, there is a concern that the conversion layer 14 may be peeled off from the TFT substrate 12. Particularly, an end part of the conversion layer 14 is easily peeled off from the TFT substrate 12.

Additionally, the present invention is not limited to a case where the TFT substrate 12 is peeled from the support body 400. Even in a case where the radiation detector 10 is handled as a single body during a manufacturing process of the radiographic imaging apparatus 1, there is a concern that the conversion layer 14 may be peeled off from the TFT substrate 12 due to the bending of the TFT substrate 12. In contrast, in the radiation detector 10 of the present embodiment, the reinforcing substrate 40 containing a material having a yield point and having a higher stiffness than the base material 11 is provided on the first surface 19A that is a surface facing the first surface 12A of the TFT substrate 12. For that reason, according to the radiation detector 10 of the present embodiment, it is possible to suppress that the TFT substrate 12 is largely bent and it is possible to suppress that the conversion layer 14 is peeled off from the TFT substrate 12.

Additionally, as described above, a flexible substrate such as polyimide has a lower thermal conductivity and a higher specific heat than a glass substrate. Therefore, in the manufacturing process of the radiation detector 10, heat does not escape easily in a case where the heat is applied to the flexible substrate. Additionally, in a case where the radiographic imaging apparatus 1 having the built-in radiation detector 10 is used, the heat is likely to stay on the flexible substrate and the temperature tends to rise. In a case where the temperature of the flexible substrate rises, thermal expansion occurs and the flexible substrate warps. As a result, the sensor unit layer 50 may be peeled off from the base material 11.

In contrast, in the radiation detector 10 of the present embodiment, the sensor unit layer 50 is fixed to the base material 11 by the fixing layer 13. For this reason, in the radiation detector 10 of the present embodiment, it is possible to suppress the occurrence of peeling of the sensor unit layer 50 off from the base material 11.

Additionally, in the radiation detector 10 of the present embodiment, the fixing layer 13 contains a resin. Thus, the weight of the radiation detector 10 can be reduced as compared to a case where the fixing layer 13 is made of metal or the like.

Particularly, in the radiation detector 10 of the present embodiment, the fixing layer 13 fixes the sensor unit layer 50 to the base material 11 at the end part of the sensor unit layer 50. Thus, a bottom surface part of the sensor unit layer 50 can be efficiently fixed to the base material 11 than in a case where the bottom surface part is fixed directly.

Moreover, in the radiation detector 10 of the present embodiment, the fixing layer 13 covers a region ranging formed from the entire surface of the sensor unit layer 50 on the conversion layer 14 side via an end surface of the sensor unit layer 50 to the surface of the base material 11 on the sensor unit layer 50 side, thereby fixing the sensor unit layer 50 to the base material 11. For this reason, the sensor unit layer 50 can be more firmly fixed to the base material 11 as compared to a case where the fixing layer 13 covers only a partial region of the surface of the sensor unit layer 50 on the conversion layer 14 side.

Second Embodiment

Next, a second embodiment will be described. A cross-sectional view of an example of the radiation detector 10 of the present embodiment is illustrated in FIG. 9.

Figure 9:
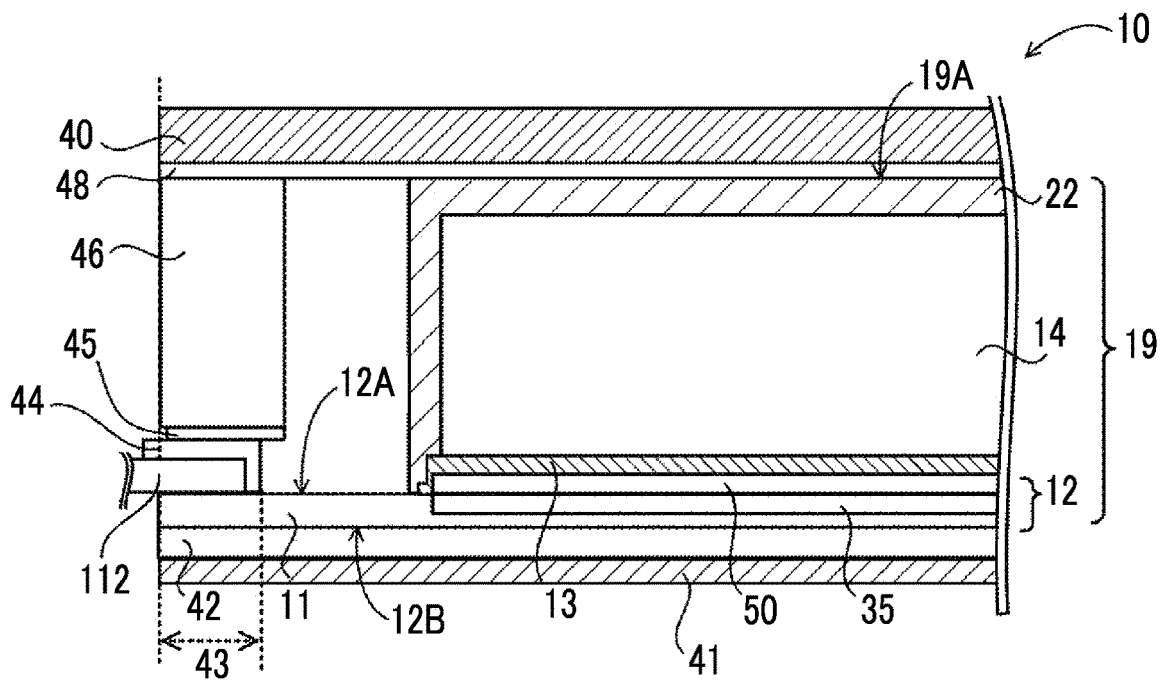
FIG. 9 is a cross-sectional view of an example of a radiation detector of a second embodiment.

As illustrated in FIG. 9, in the radiation detector 10 of the present embodiment, a reinforcing member 41 is provided on the second surface 12B on the TFT substrate 12 side. In the radiation detector 10 of the present embodiment, as illustrated in FIG. 9, the protective film 42 is provided between the TFT substrate 12 and the reinforcing member 41, similar to the above embodiment.

Similar to the reinforcing substrate 40, the reinforcing member 41 has a higher stiffness than the base material 11, and a dimensional change (deformation) due to a force applied in a direction perpendicular to the first surface 12A is smaller than a change in dimension due to the force applied perpendicular to the second surface 12B of the base material 11. Additionally, the thickness of the reinforcing member 41 of the present embodiment is larger than the thickness of the base material 11 and smaller than the thickness of the reinforcing substrate 40. The material of the reinforcing member 41 of the present embodiment is preferably a thermoplastic resin, and the same material as the reinforcing substrate 40 can be used. In addition, the stiffness referred to herein also means the difficulty of bending the reinforcing member 41 and the base material 11 including the thickness of the reinforcing member 41 and the base material 11, and means that the higher the stiffness, the more difficult it is to bend. The bending elastic modulus of the reinforcing member 41 is also preferably 1000 MPa or more and 2500 MPa or less, similar to the reinforcing substrate 40.

In addition, the reinforcing member 41 may be further reinforced with an additional reinforcing member, and the additional reinforcing member may be, for example, a rigid plate such as a carbon plate. Even in a case where the entire surface of the conversion layer 14 is covered with the additional reinforcing member, in a case where the material of the additional reinforcing member is carbon or the like having a small amount of X-ray absorption, X-ray loss can be suppressed in both the irradiation side sampling type and the penetration side sampling type. Here, the X-ray loss means that the emitted X-rays are absorbed by the additional reinforcing member, and thereby, the X-rays reaching the conversion layer 14 are reduced. The additional reinforcing member has a bending elastic modulus larger than that of the reinforcing member 41. The bending elastic modulus of the additional reinforcing member is preferably, for example, 8,000 MPa or more. Additionally, an upper limit of the bending elastic modulus of the additional reinforcing member is preferably 60,000 MPa or less. In addition, the bending elastic modulus of carbon is about 8,000 MPa to 50,000 MPa, and carbon is suitable as the additional reinforcing member from the viewpoint of the bending elastic modulus.

In the radiation detector 10 of the present embodiment, for example, the TFT substrate 12 is peeled off from the support body 400 after the reinforcing substrate 40 provided with the spacer 46 is bonded to the TFT substrate 12 provided with the laminate 19 by the same method of manufacturing as the method of manufacturing the radiation detector 10 described above in the first embodiment. Thereafter, the radiation detector 10 of the present embodiment can be manufactured by providing the protective film 42 and the reinforcing member 41 on the second surface 12B of the TFT substrate 12 by application or the like.

In the radiation detector 10 of the present embodiment, the reinforcing member 41 having a higher stiffness than the base material 11 is provided on the second surface 12B of the TFT substrate 12 facing the first surface 12A on which the sensor unit layer 50 is formed. For that reason, compared to the radiation detector 10 of the first embodiment, it is possible to further suppress that the TFT substrate 12 is largely bent and it is possible to further suppress that the conversion layer 14 and the sensor unit layer 50 are peeled off from the TFT substrate 12.

Additionally, for example, in a case where the difference between the coefficient of thermal expansion of the conversion layer 14 and the coefficient of thermal expansion of the reinforcing substrate 40 is relatively large, the TFT substrate 12 is likely to warp. In contrast, in the radiation detector 10 of the present embodiment, the TFT substrate 12 is sandwiched between the reinforcing substrate 40 and the reinforcing member 41. Therefore, it is possible to suppress that the TFT substrate 12 warps due to a difference in coefficient of thermal expansion or the like.

Third Embodiment

In each of the above embodiments, a form has been exemplified in which the fixing layer 13 as the fixing member of the present disclosure covers the entire surface of the sensor unit layer 50 on the conversion layer 14 side. However, the fixing member of the present disclosure is not limited to this form. For example, as the fixing member, a form may be adopted in which the fixing layer 13 covers a region ranging formed from a portion of the entire of the sensor unit layer 50 on the conversion layer 14 side via an end surface of the sensor unit layer 50 to a portion of the surface of the base material 11 on the sensor unit layer 50 side, thereby fixing the sensor unit layer 50 to the base material 11.

Figure 10:
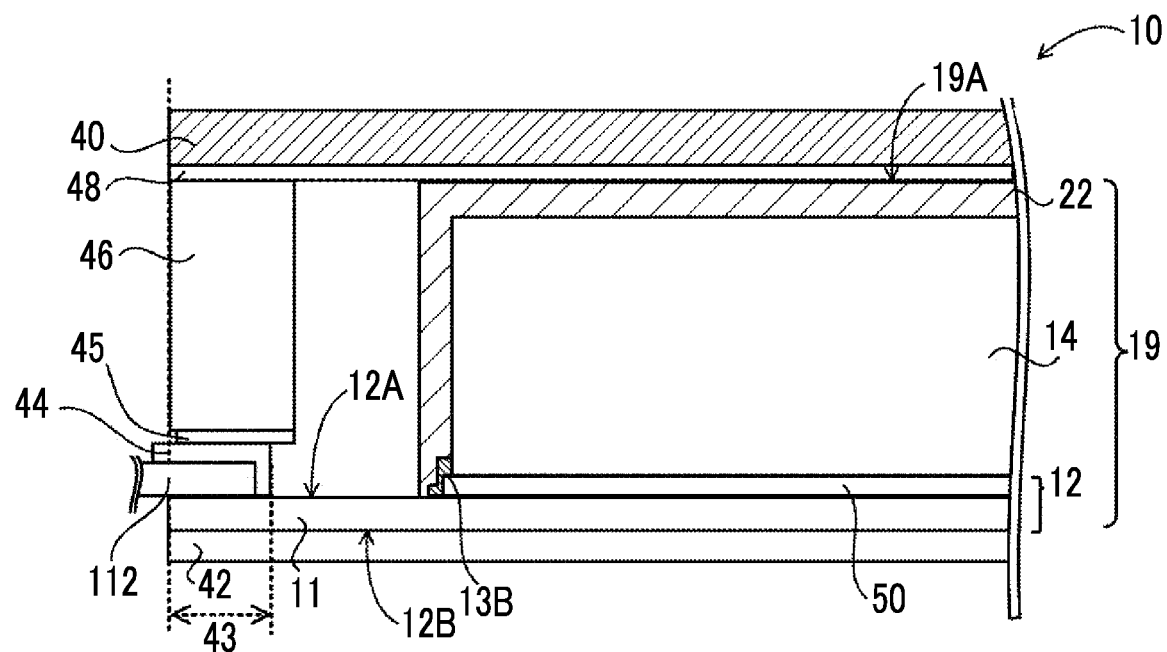
FIG. 10 is a cross-sectional view of an example of a radiation detector of a third embodiment.

A cross-sectional view of an example of the radiation detector 10 of the present embodiment is illustrated in FIG. 10. In addition, the same constituent elements in FIG. 10 as those in FIG. 4 are designated by the same reference signs as those in FIG. 4, and the description thereof will be omitted.

As illustrated in FIG. 10, the radiation detector 10 according to the present embodiment is different only in that a fixing member 13B that covers only the vicinity of the outer peripheral part of the sensor unit layer 50 with respect to the surface of the sensor unit layer 50 on the conversion layer 14 side is used instead of the fixing layer 13 in the radiation detector 10 of the first embodiment.

In the radiation detector 10 according to the present embodiment, as illustrated in FIG. 10, the fixing member 13B has a position outside the outer peripheral part of the conversion layer 14 as the position of an end part of the surface of the sensor unit layer 50 on the conversion layer 14 side. For this reason, the conversion layer 14 according to the present embodiment is directly formed on an upper surface of the sensor unit layer 50. However, the present invention is not limited to this form, and the fixing member 13B may have a position inside the outer peripheral part of the conversion layer 14 as the position of the end part on the surface of the sensor unit layer 50 on the conversion layer 14 side. In addition, since the method of forming the fixing member 13B in the present embodiment is the same as that of the fixing layer 13 according to each of the above embodiments, the description thereof herein will be omitted.

Figure 11:
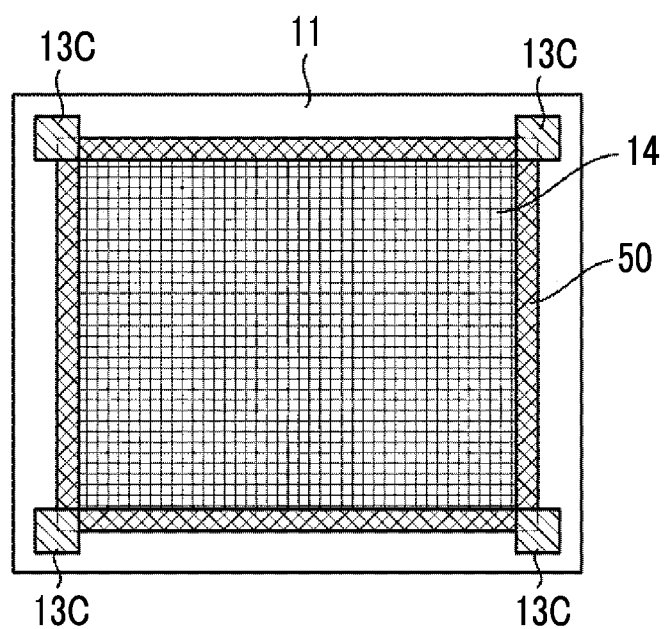
FIG. 11 is a plan view of another example of the radiation detector of the third embodiment.
Figure 12:
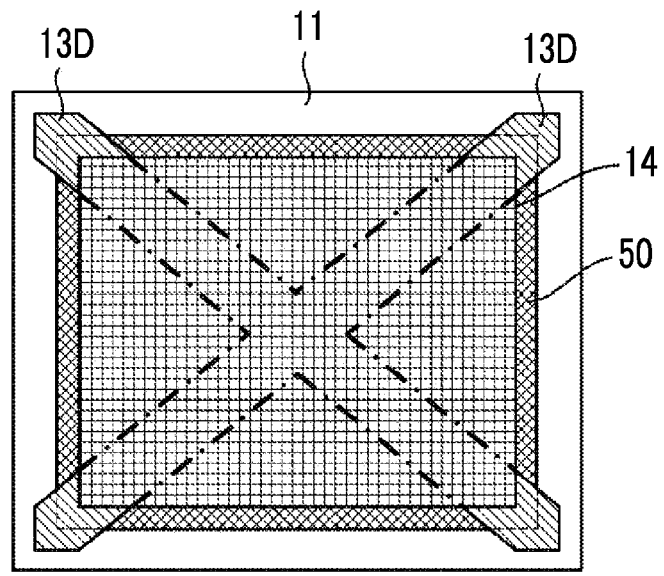
FIG. 12 is a plan view of another example of the radiation detector of the third embodiment.

FIGS. 11 and 12 illustrate modification examples of the fixing member 13B according to the third embodiment. In addition, FIGS. 11 and 12 are plan views of the radiation detector 10 as viewed from the reinforcing substrate 40 side. Additionally, in FIGS. 11 and 12, only the main parts (the base material 11, the fixing member 13C (13D), the sensor unit layer 50, and the conversion layer 14) of the radiation detector 10 are illustrated in order to avoid complications.

The example illustrated in FIG. 11 has a form in which a fixing member 13C individually fixes only each of four corner points of the sensor unit layer 50 having a rectangular shape in a plan view. Additionally, in the example illustrated in FIG. 12, a fixing member 13D is provided in an X shape in a plan view so as to extend between the diagonals of the sensor unit layer 50 having a rectangular shape in the plane view. In addition, the positions of the end parts of the fixing member 13C and the fixing member 13D on the base material 11 side are the same as those of the fixing layer 13 according to each of the above embodiments. Since the method of forming the fixing member 13C (13D) in this form is also the same as that of the fixing layer 13 according to each of the above embodiments, the description thereof herein will be omitted.

In the third embodiment, in the forms illustrated in FIGS. 11 and 12, the fixing member covers a region ranging formed from a portion of the surface of the sensor unit layer 50 on the conversion layer 14 side via an end surface of the sensor unit layer 50 to the surface of the base material 11 on the sensor unit layer 50 side, thereby fixing the sensor unit layer 50 to the base material 11. For this reason, the image quality of a radiographic image obtained by the radiation detector 10 can be improved as compared to a case where the fixing layer 13 covers the entire surface of the sensor unit layer 50 on the conversion layer 14 side.

Figure 13:
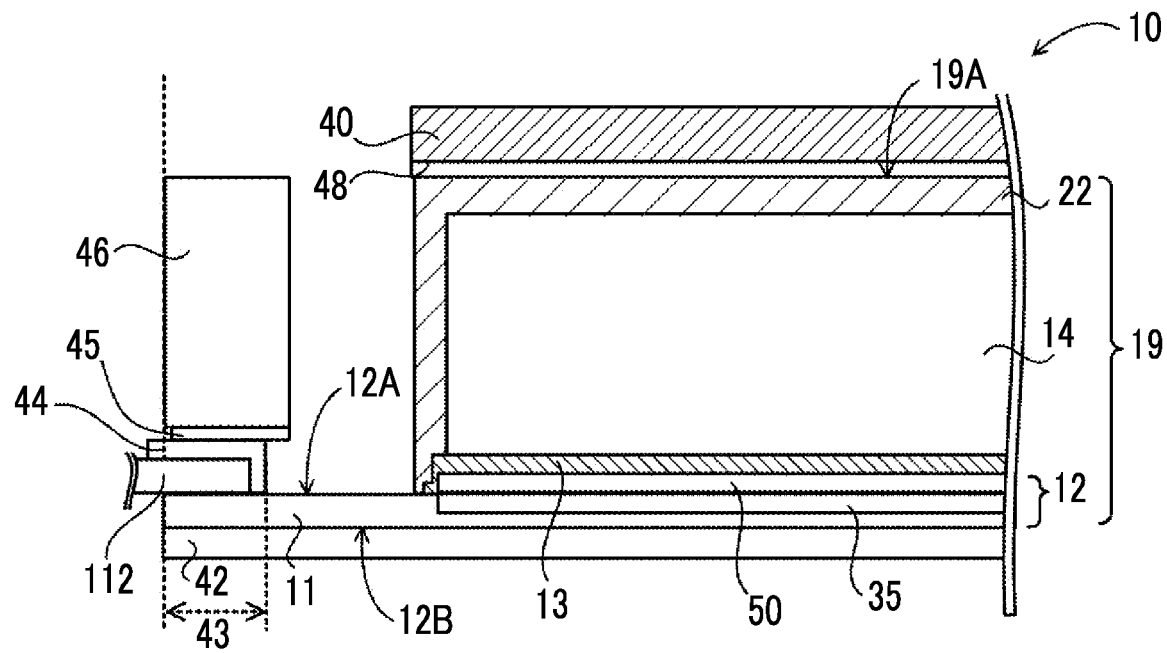
FIG. 13 is a cross-sectional view of another example of the radiation detector of the embodiment.

In addition, the size of the reinforcing substrate 40 is not limited to each of the above embodiments. For example, as in the example illustrated in FIG. 13, the end parts (outer peripheries) of the reinforcing substrate 40 and the pressure sensitive adhesive layer 48 and the end part (outer periphery) of the protective layer 22 may be at the same position. In addition, it is preferable that the reinforcing substrate 40 covers a region wider than the region where the conversion layer 14 covers the first surface 12A of the TFT substrate 12, and it is more preferable that the reinforcing substrate 40 covers a region wider than the region where the conversion layer 14 covers the entire upper surface of the conversion layer 14.

Figure 14:
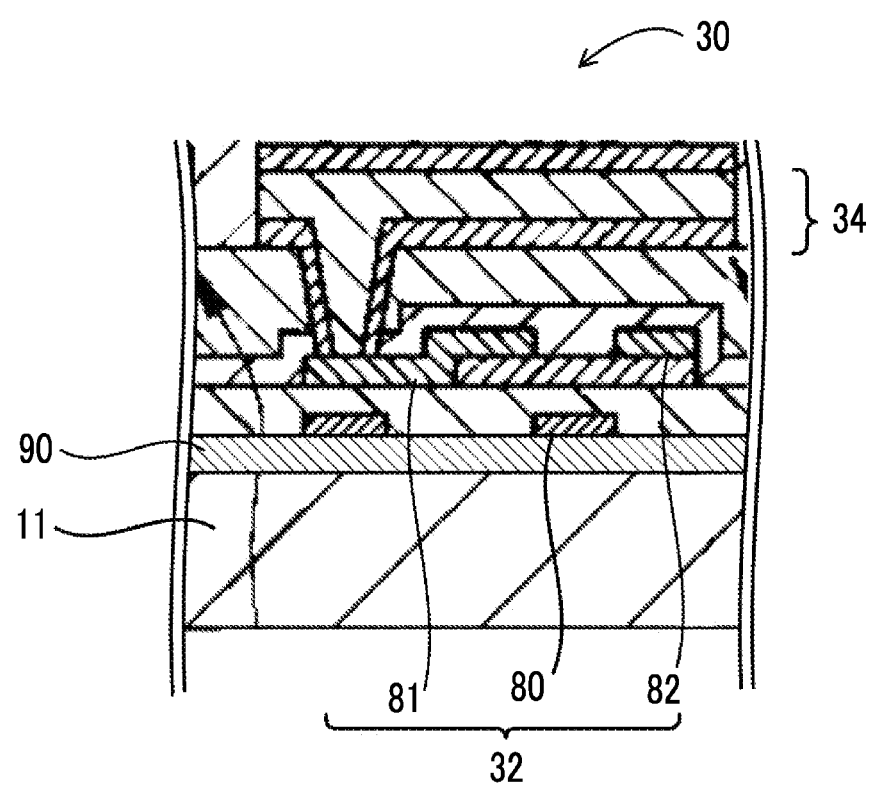
FIG. 14 is a cross-sectional view of one pixel portion of another example of the radiation detector of the embodiment.

Additionally, as in the example illustrated in FIG. 14, it is preferable that a layer 90 made of an inorganic material is provided between the base material 11 and a pixel 30, particularly a gate electrode 80 of the TFT 32 of the pixel 30. Examples of the inorganic material in the case of the example illustrated in FIG. 14 include SiNx and SiOx. A drain electrode 81 of the TFT 32 and a source electrode 82 are formed in the same layer, and the gate electrode 80 is formed between a layer on which the drain electrode 81 and the source electrode 82 are formed and the base material 11. Additionally, the layer 90 made of an inorganic material is provided between the base material 11 and the gate electrode 80.

Additionally, in the above respective embodiments, as illustrated in FIG. 1, an aspect in which the pixels 30 are two-dimensionally arranged in a matrix has been described. However, the invention is not limited to the aspect, and for example, the pixels 30 may be one-dimensionally arranged or may be arranged in a honeycomb shape. Additionally, the shape of the pixels is also not limited, and may be a rectangular shape, or may be a polygonal shape, such as a hexagonal shape. Moreover, the shape of the sensor unit layer 50 is not limited.

Additionally, the shape or the like of the conversion layer 14 is not limited to the above respective embodiments. In the above respective embodiments, an aspect in which the shape of the conversion layer 14 is a rectangular shape like the shape of the sensor unit layer 50 has been described. However, the shape of the conversion layer 14 may not be the same shape as the sensor unit layer 50. Additionally, the shape of the sensor unit layer 50 may not be a rectangular shape, but may be, for example, other polygonal shapes or a circular shape.

Additionally, in the above-described method of manufacturing the radiation detector 10, the step of peeling the TFT substrate 12 off from the support body 400 by the mechanical peeling has been described. However, the peeling method is not limited to the described form. For example, a form of performing so-called laser peeling of peeling the TFT substrate 12 by emitting a laser beam from the surface of the support body 400 opposite to the side on which the TFT substrate 12 is formed may be adopted. Even in this case, according to the radiation detector 10, in a case where the radiation detector 10 is handled as a single body after the TFT substrate 12 is peeled off from the support body 400, it is possible to suppress that the conversion layer 14 and the sensor unit layer 50 are peeled off from the TFT substrate 12.

In addition, the radiation detector 10 of each of the above embodiments may be applied to a irradiation side sampling type radiographic imaging apparatus in which radiation is emitted from the TFT substrate 12 side, or may be applied to a penetration side sampling type radiographic imaging apparatus in which radiation is emitted from the conversion layer 14 side.

Figure 15:
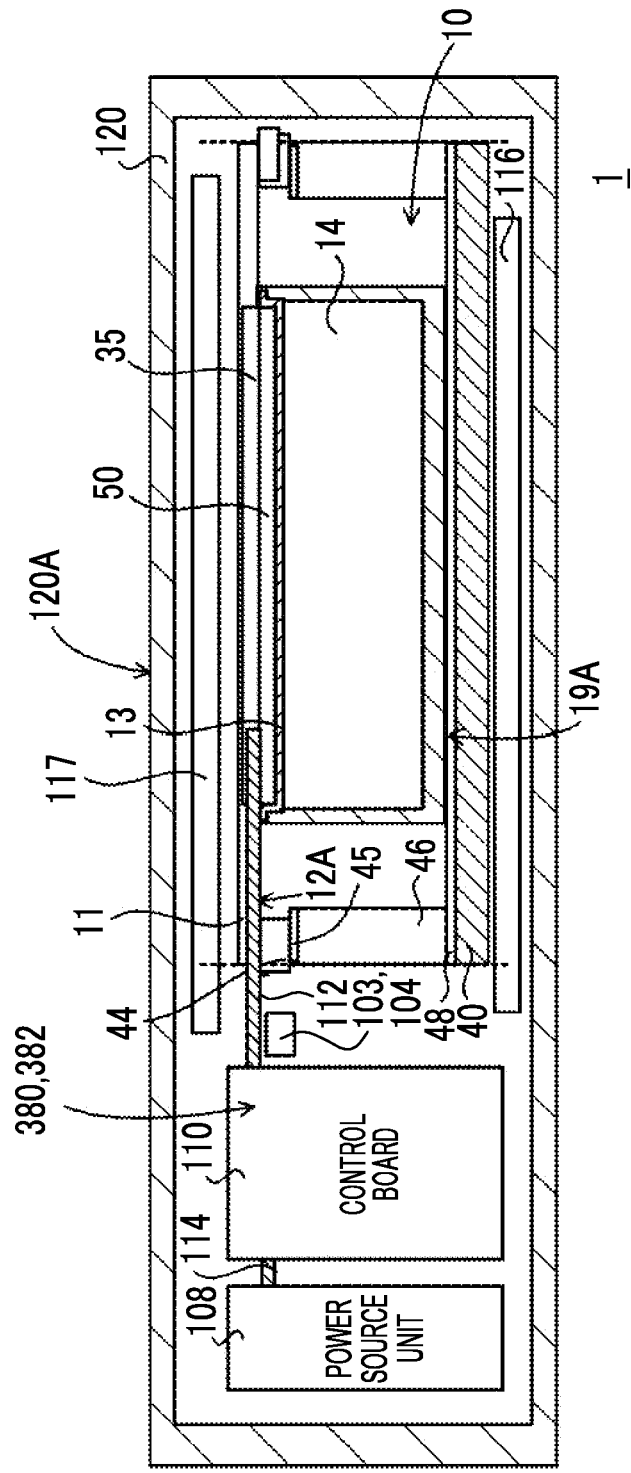
FIG. 15 is a cross-sectional view illustrating the cross section of an example of a radiographic imaging apparatus to which the radiation detector of the embodiment is applied.

A cross-sectional view of an example in a state where the radiation detector 10 of the first embodiment is applied to a irradiation side sampling type radiographic imaging apparatus 1 is illustrated in FIG. 15.

As illustrated in FIG. 15, the radiation detector 10, the power source unit 108, and a control board 110 are provided side by side in a direction intersecting an incidence direction of radiation within the housing 120. The radiation detector 10 is provided in a state where a side where the conversion layer 14 of the sensor unit layer 50 is not provided faces an imaging surface 120A side of the housing 120 that is irradiated with radiation transmitted through the subject.

The control board 110 is a board in which an image memory 380 for storing image data according to the electric charges read from the pixels 30 of the sensor unit layer 50, a control unit 382 for controlling reading or the like of the electric charges from the pixels 30, and the like are formed, and is electrically connected to the pixels 30 of the sensor unit layer 50 by a flexible cable 112 including a plurality of signal wiring lines. In addition, in the radiographic imaging apparatus 1 illustrated in FIG. 15 the control board 110 is a so-called chip on film (COF) in which a drive unit 103 for controlling the switching states of the TFTs 32 of the pixels 30 under the control of the control unit 382, and a signal processing unit 104 for creating and outputting image data according to the electric charges read from the pixels 30 are provided on the flexible cable 112. However, at least one of the drive unit 103 or the signal processing unit 104 may be formed in the control board 110.

Additionally, the control board 110 is connected to the power source unit 108, which supplies electrical power to the image memory 380, the control unit 382, and the like that are formed in the control board 110, by a power source line 114. In addition, the control unit 382 includes a hardware processor. The processor may be a central processing unit (CPU) or the like that functions by loading and executing a control program from a memory such as a read only memory (ROM) or an application specific integrated circuit (ASIC) or the like of which the functions are set in advance).

A sheet 116 is further provided on a side from which the radiation transmitted through the radiation detector 10 is emitted, within the housing 120 of the radiographic imaging apparatus 1 illustrated in FIG. 15. The sheet 116 is, for example, a copper sheet. The copper sheet does not easily generate secondary radiation due to incident radiation, and thereby, has a function of preventing scattering to the rear side, that is, the conversion layer 14 side. In addition, the sheet 116 preferably covers at least an entire surface of the conversion layer 14 from which radiation is emitted, and more preferably covers the entire conversion layer 14.

Additionally, a protective layer 117 is further provided on a side (imaging surface 120A side) to which radiation is incident, within the housing 120 of the radiographic imaging apparatus 1 illustrated in FIG. 15. As the protective layer 117, moistureproof films, such as an ALPET (registered trademark) sheet obtained by laminating aluminum, for example by adhering aluminum foil, to the insulating sheet (film), a Parylene (registered trademark) film, and an insulating sheet (film), such as polyethylene terephthalate, can be applied. The protective layer 117 has a moistureproof function and an antistatic function with respect to the sensor unit layer 50. For that reason, it is preferable that the protective layer 117 covers at least the entire surface of the sensor unit layer 50 on the side to which radiation is incident, and it is preferable to cover the entire surface of the TFT substrate 12 on the side to which radiation is incident.

In addition, although FIG. 15 illustrates a form in which both the power source unit 108 and the control board 110 are provided on one side of the radiation detector 10, specifically, on one side of a rectangular sensor unit layer 50, a position where the power source unit 108 and the control board 110 are provided is not limited to the form illustrated in FIG. 15. For example, the power source unit 108 and the control board 110 may be provided so as to be respectively decentralized onto two facing sides of the sensor unit layer 50 or may be provided so as to be respectively decentralized onto two adjacent sides.

Figure 16:
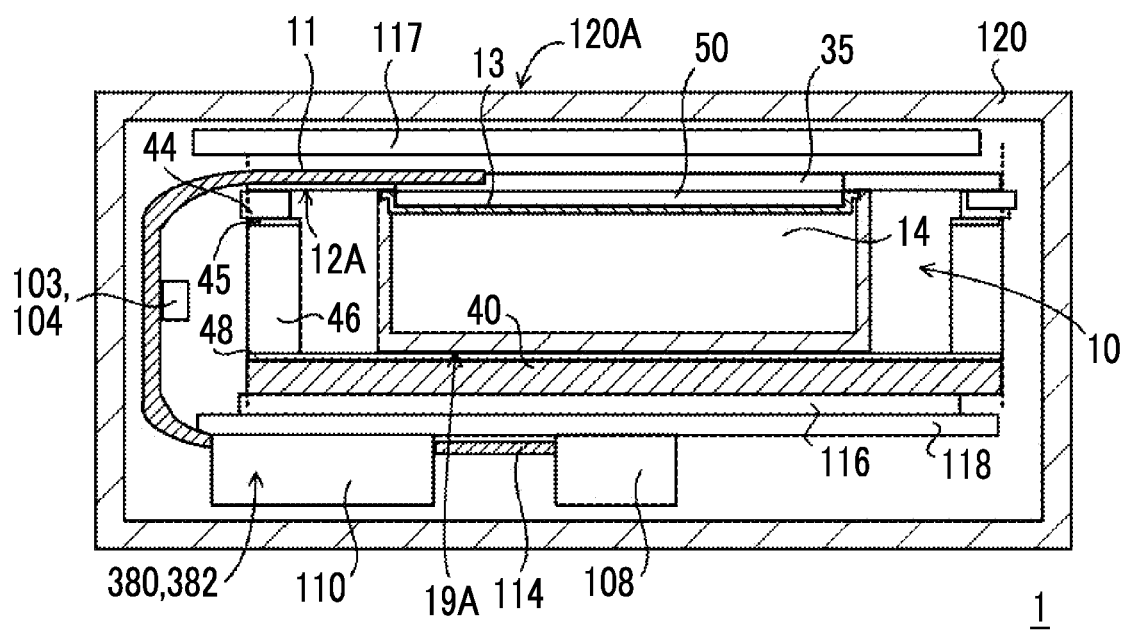
FIG. 16 is a cross-sectional view illustrating the cross section of another example of the radiographic imaging apparatus to which the radiation detector of the embodiment is applied.

Additionally, a cross-sectional view of another example in a state where the radiation detector 10 of the first embodiment is applied to the irradiation side sampling type radiographic imaging apparatus 1 is illustrated in FIG. 16.

As illustrated in FIG. 16, the power source unit 108 and the control board 110 are provided side by side in the direction intersecting the incidence direction of radiation within the housing 120, and the radiation detector 10, the power source unit 108, and the control board 110 are provided side by side in the incidence direction of radiation.

Additionally, in the radiographic imaging apparatus 1 illustrated in FIG. 16, a base 118 that supports the radiation detector 10 and the control board 110 is provided between the control board 110 and the power source unit 108, and the sheet 116. For example, carbon or the like is used for the base 118.

In addition, the configurations, manufacturing methods, and the like of the radiation detectors 10, and the like that are described in the above respective embodiments are merely examples, and can be modified in accordance with situations without departing from the scope of the present invention.

The present application claims the priority of Japanese Application No. 2018-182729 filed on Sep. 27, 2018, which is incorporated herein in its entirety by reference.

An object of the present disclosure is to provide a radiation detector, a radiographic imaging apparatus, and a manufacturing method capable of suppressing the occurrence of peeling of a sensor unit layer off from a base material in a radiation detector.

A radiation detector of a first aspect of the present disclosure includes a substrate including a sensor unit layer having a plurality of pixels for accumulating electric charges generated depending on light converted from radiation in a pixel region of a flexible base material; a conversion layer that is provided on a surface side of the base material provided with the pixel region to convert the radiation into light; and a fixing member that is provided closer to the substrate side than the conversion layer to fix the sensor unit layer to the base material.

The radiation detector of a second aspect of the present disclosure is the radiation detector of the first aspect in which the fixing member is configured to contain a resin.

The radiation detector of a third aspect of the present disclosure is the radiation detector of the first aspect or the radiation detector of the second aspect in which the fixing member fixes the sensor unit layer to the base material at an end part of the sensor unit layer.

The radiation detector of a fourth aspect of the present disclosure is the radiation detector of the third aspect in which the fixing member fixes the sensor unit layer to the base material by covering a region ranging from at least a portion of a surface of the sensor unit layer on the conversion layer side to at least a portion of a surface of the base material on the sensor unit layer side via an end surface of the sensor unit layer.

The radiation detector of a fifth aspect of the present disclosure is the radiation detector of the fourth aspect the fixing member fixes the sensor unit layer to the base material by covering a region ranging from an entire surface of the sensor unit layer on the conversion layer side to at least a portion of a surface of the base material on the sensor unit layer side via an end surface of the sensor unit layer.

The radiation detector of a sixth aspect of the present disclosure is the radiation detector of the fifth aspect in which the base material and the fixing member contain the same material.

The radiation detector of a seventh aspect of the present disclosure is the radiation detector of the fifth aspect or the radiation detector of the sixth aspect in which a ratio of a coefficient of thermal expansion $CTE_{flex}$ of the base material to a coefficient of thermal expansion $CTE_{sur}$ of the fixing member satisfies $0.5 \leq CTE_{sur}/CTE_{flex} \leq 4$.

The radiation detector of an eighth aspect of the present disclosure is the radiation detector of any one of the first to seventh aspects in which the base material contains polyimide.

The radiation detector of a ninth aspect of the present disclosure is the radiation detector of the eighth aspect in which the base material is formed by application.

The radiation detector of a tenth aspect of the present disclosure is the radiation detector of the eighth aspect or the radiation detector of the ninth aspect in which the fixing member contains polyimide or Parylene (registered trademark).

The radiation detector of an eleventh aspect of the present disclosure is the radiation detector of any one of the first to tenth aspects, further comprising a sealing layer that covers the conversion layer, and a material of the fixing member is different from that of the sealing layer.

The radiation detector according to a twelfth aspect of the present disclosure is the radiation detector according to any one of the first to eleventh aspects in which the conversion layer is formed by direct vapor deposition of a CsI columnar crystal, and a reinforcing substrate having a higher stiffness than the base material is further provided on a distal end part side of the columnar crystal.

The radiation detector of a thirteenth aspect of the present disclosure is the radiation detector of a twelfth aspect in which the reinforcing substrate contains a material having a yield point.

The radiation detector of a fourteenth aspect of the present disclosure is the radiation detector of the twelfth aspect or the radiation detector of the thirteenth aspect, the reinforcing substrate is provided in a region wider than a region where the conversion layer is provided.

The radiation detector of a fifteenth aspect of the present disclosure is the radiation detector of any one of the twelfth to fourteenth aspects in which a reinforcing member having a higher stiffness than the base material is further provided on a surface of the substrate facing a surface provided with the pixel region.

Additionally, a radiographic imaging apparatus of a sixteenth aspect of the present disclosure comprises the radiation detector according to any one of the first a to fifteenth aspects; a control unit that outputs a control signal for reading out electric charges accumulated in the plurality of pixels; and a circuit unit that is electrically connected to the radiation detector by a flexible wiring line to read out the electric charges from the plurality of pixels according to the control signal.

Additionally, a manufacturing method of a seventeenth aspect of the present disclosure is a method of manufacturing a radiation detector, comprising providing a flexible base material on a support body via a peeling layer and forming a substrate provided with a sensor unit layer having a plurality of pixels for accumulating electric charges generated depending on light converted from radiation, in a pixel region of the base material; forming a fixing member that fixes the sensor unit layer to the base material; forming a conversion layer for converting the radiation into light on a surface side of the base material provided with the pixel region; and bonding a reinforcing substrate having a higher stiffness than the base material to a surface of the conversion layer opposite to a surface facing the substrate side; and peeling a substrate provided with the conversion layer and the reinforcing substrate off from the support body.

According to the present disclosure, it is possible to suppress the occurrence of peeling of the sensor unit layer off from the base material in the radiation detector.

What is claimed is:

1. A radiation detector comprising:
a substrate including a sensor unit layer having a plurality of pixels for accumulating electric charges generated depending on light converted from radiation in a pixel region of a flexible base material;
a conversion layer that is provided on a surface side of the base material provided with the pixel region to convert the radiation into light; and
a fixing member that is provided closer to the substrate side than the conversion layer to fix the sensor unit layer to the base material, wherein
the fixing member fixes the sensor unit layer to the base material at an end part of the sensor unit layer, and
the fixing member fixes the sensor unit layer to the base material by covering a region ranging from at least a portion of a surface of the sensor unit layer on the conversion layer side to at least a portion of a surface of the base material on the sensor unit layer side via an end surface of the sensor unit layer.

2. The radiation detector according to claim 1,
wherein the fixing member is configured to contain a resin.

3. The radiation detector according to claim 1,
wherein the fixing member fixes the sensor unit layer to the base material by covering a region ranging from an entire surface of the sensor unit layer on the conversion layer side to at least a portion of a surface of the base material on the sensor unit layer side via an end surface of the sensor unit layer.

4. The radiation detector according to claim 3,
wherein the base material and the fixing member contain the same material.

5. The radiation detector according to claim 3,
wherein a ratio of a coefficient of thermal expansion $CTE_{flex}$ of the base material to a coefficient of thermal expansion $CTE_{sur}$ of the fixing member satisfies $0.5 \leq CTE_{sur}/CTE_{flex} \leq 4$.

6. The radiation detector according to claim 1,
wherein the base material contains polyimide.

7. The radiation detector according to claim 6,
wherein the base material is formed by application.

8. The radiation detector according to claim 6,
wherein the fixing member contains polyimide or Parylene (registered trademark).

9. The radiation detector according to claim 1, further comprising:
a sealing layer that covers the conversion layer,
wherein a material of the fixing member is different from that of the sealing layer.

10. The radiation detector according to claim 1,
wherein the conversion layer is formed by direct vapor deposition of a CsI columnar crystal, and
a reinforcing substrate having a higher stiffness than the base material is further provided on a distal end part side of the columnar crystal.

11. The radiation detector according to claim 10,
wherein the reinforcing substrate contains a material having a yield point.

12. The radiation detector according to claim 10,
wherein the reinforcing substrate is provided in a region wider than a region where the conversion layer is provided.

13. The radiation detector according to claim 10,
wherein a reinforcing member having a higher stiffness than the base material is further provided on a surface of the substrate facing a surface provided with the pixel region.

14. A radiographic imaging apparatus comprising:
a radiation detector including:
a substrate including a sensor unit layer having a plurality of pixels for accumulating electric charges generated depending on light converted from radiation in a pixel region of a flexible base material;
a conversion layer that is provided on a surface side of the base material provided with the pixel region to convert the radiation into light; and
a fixing member that is provided closer to the substrate side than the conversion layer to fix the sensor unit layer to the base material;

a control unit that outputs a control signal for reading out electric charges accumulated in the plurality of pixels; and a circuit unit that is electrically connected to the radiation detector by a flexible wiring line to read out the electric charges from the plurality of pixels according on the control signal, wherein the fixing member fixes the sensor unit layer to the base material at an end part of the sensor unit layer, and the fixing member fixes the sensor unit layer to the base material by covering a region ranging from at least a portion of a surface of the sensor unit layer on the conversion layer side to at least a portion of a surface of the base material on the sensor unit layer side via an end surface of the sensor unit layer.

15. A method of manufacturing a radiation detector, comprising:

providing a flexible base material on a support body via a peeling layer and forming a substrate provided with a sensor unit layer having a plurality of pixels for accumulating electric charges generated depending on light converted from radiation, in a pixel region of the base material;

forming a fixing member that fixes the sensor unit layer to the base material;

forming a conversion layer for converting the radiation into light on a surface side of the base material provided with the pixel region; and bonding a reinforcing substrate having a higher stiffness than the base material to a surface of the conversion layer opposite to a surface facing the substrate side; and peeling a substrate provided with the conversion layer and the reinforcing substrate off from the support body.

* * * * *